United States Patent [19]

Menassa et al.

[11] Patent Number: 5,338,511

[45] Date of Patent: Aug. 16, 1994

[54] UNDECYLENATE DEODORANTS FOR SEWAGE SLUDGES

[75] Inventors: Aime Menassa, Paris; Henri Caupin, Versailles, both of France

[73] Assignees: Delta Agro Industries, Paris; Atochem, Puteaux, both of France

[21] Appl. No.: 630,181

[22] Filed: Dec. 19, 1990

[30] Foreign Application Priority Data

Dec. 19, 1989 [FR] France ................ 89 16792

[51] Int. Cl.$^5$ .............................................. A61L 9/01
[52] U.S. Cl. ......................................... 422/5; 210/749; 210/751
[58] Field of Search .................... 422/5; 210/749, 751, 210/916

[56] References Cited

U.S. PATENT DOCUMENTS

| | | | |
|---|---|---|---|
| 3,091,511 | 5/1963 | Calhoun | 422/5 |
| 3,953,377 | 4/1976 | Naf | 512/26 |
| 3,989,498 | 11/1976 | Cox | 210/916 |
| 4,649,046 | 3/1987 | Kross | 424/76.4 |
| 4,938,416 | 7/1990 | Bertrand et al. | 239/1 |

OTHER PUBLICATIONS

Price, E. C., "Sewage Treatment Plants Combat Odor Problems", *Water and Sewage Works*, Oct. 1978, pp. 64–69.

C. Duval & R. Duval, *Dictionnaire de la Chimie et de ses Applications*, 3rd Edition, p. 1043.

*The Merck Index*, 9th Edition, 1976, p. 9505.

*Aldrich*, 1990, p. 1323.

Primary Examiner—Timothy M. McMahon
Attorney, Agent, or Firm—Burns, Doane, Swecker & Mathis

[57] ABSTRACT

Malodorous sewage sludges are deodorized by treating same with an effective deodorizing amount of at least one alkyl or polyoxyalkylene ester of undecylenic acid.

8 Claims, 2 Drawing Sheets

UNDECYLENATE DEODORANTS FOR SEWAGE SLUDGES

CROSS-REFERENCE TO COMPANION APPLICATIONS

Copending applications U.S. Ser. No. 07/630,183 now abandoned and U.S. Ser. No. 07/629,848 now abandoned both filed concurrently herewith and both assigned to the assignee hereof.

BACKGROUND OF THE INVENTION

1. Field of the Invention

The present invention relates to the deodorization of sludges emanating from sewage plants, and, more especially, to the deodorization of such sewage by treating same with an effective deodorizing amount of at least one alkyl or polyoxyalkylene ester of undecylenic acid.

2. Description of the Prior

Sewage treatment plants are notorious sources of malodorous pollutants, which originate in the effluents both upstream and downstream of the treatment facility.

Upstream of the plant, drains constitute sites of fermentation influenced by the effluent temperature, the velocity of the water, the type of sewage system, etc.

The odor emissions are not well retained within the treatment facility.

The reduction of the risks of emission is a primary measure in combatting objectionable odors and typically such measure entails:

(i) the elimination of volatile pollutants contained in the effluents;

(ii) the limitation of the phenomenon of formation of malodorous chemical compounds;

(iii) the limitation of the physical phenomenon of conversion of aqueous phases into gaseous phases.

Deodorization also typically entails treatment of the sewage, upstream of the sewage plant, by means of at least one of the following techniques:

(a) injecting hydrogen peroxide into the sewage;

(b) injecting pure oxygen into the sewage;

(c) injecting iron salts (ferrous sulfate complexing sulfides in the form of iron sulfide) into the sewage.

In actual fact, the principal sources of uncontrolled odors in sewage plants are associated with the formation of sludges.

SUMMARY OF THE INVENTION

Accordingly, a major object of the present invention is the provision of novel technique for the deodorization of sewage sludges, comprising treating such sludges with an effective deodorizing amount of an alkyl or polyoxyalkylene ester of undecylenic acid.

DETAILED DESCRIPTION OF PREFERRED EMBODIMENTS OF THE INVENTION

More particularly according to the present invention, the preferred alkyl esters have from 1 to 12 carbon atoms in their ester moieties and the preferred polyoxyalkylene esters of undecylenic acid contain from 2 to 10 oxyalkylene recurring units, more preferably the polyoxyethylene, polyoxypropylene and poly(oxyethylene)/(oxypropylene such esters.

The deodorants according to the invention may comprise a single such ester of undecylenic acid, or a mixture thereof, and such esters may be used neat or in the form of a solution or suspension thereof, or they may be adsorbed onto any suitable support, such as, for example, clay particles.

In general, the undecylenic acid esters are effective as deodorants in very small amounts, for example on the order of 0.01% to 5% by weight relative to the weight of the sludge to be deodorized.

The Figures of Drawing are graphs illustrating the effectiveness, for purposes of deodorization, of certain alkyl and polyoxyethylene esters of undecylenic acid according to the invention.

On the curves, the abscissa represents the amount of the undecylenic acid ester incorporated, in percent by weight, and the ordinate represents the degree of the olfactory perception of odor, with the values of 1 to 6 respectively representing: none, very weak, weak, intermediate, strong and very strong.

In said Figures of Drawing, the top curve corresponds to the odor of the sludge itself and the lower curve, if present, the odor of the ester.

Figure 1:
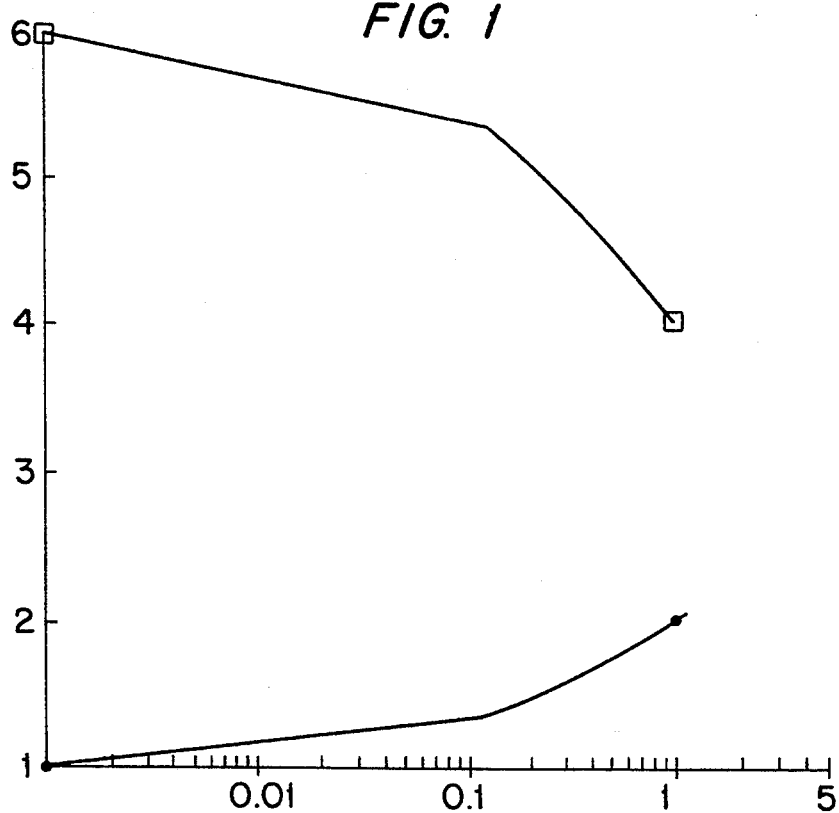
FIGS. 1-4 are graphs showing the effectiveness of certain esters.
Figure 2:
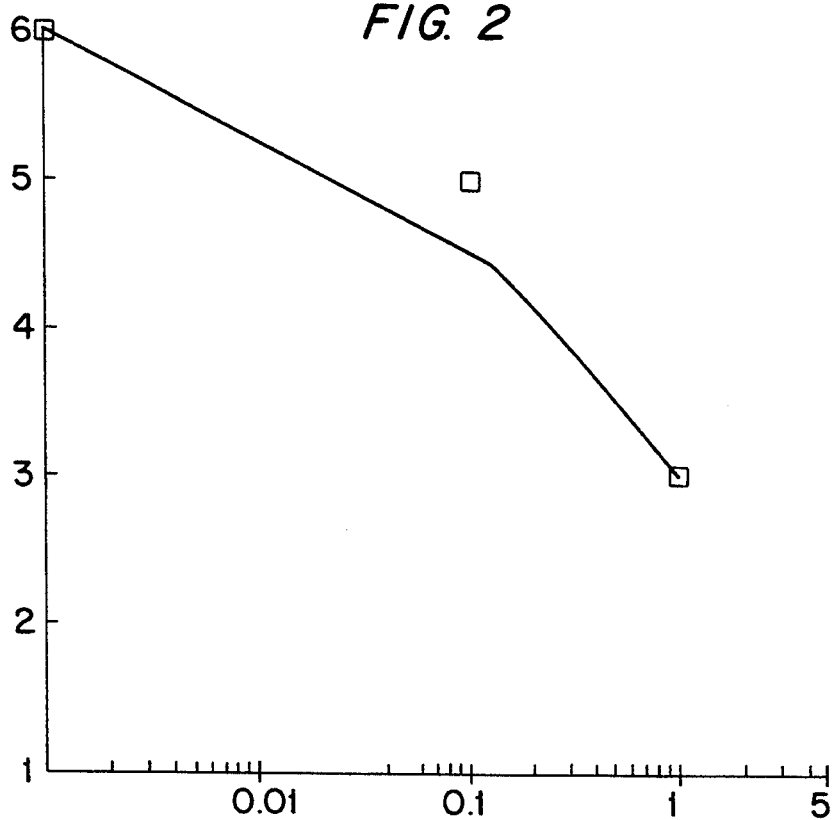
Figure 3:
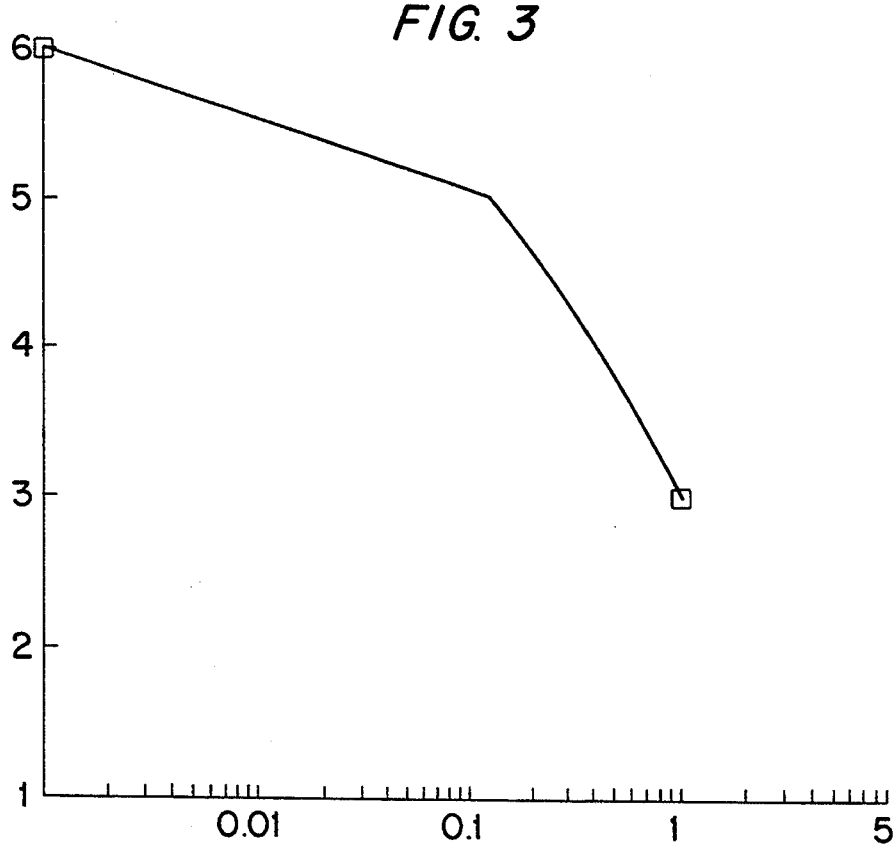

The curves of FIGS. 1 to 3, according to the invention, evidence that the reduction of the perception of the odor of the sludge is not replaced appreciably by the perception of an odor emanating from the ester itself.

Figure 4:
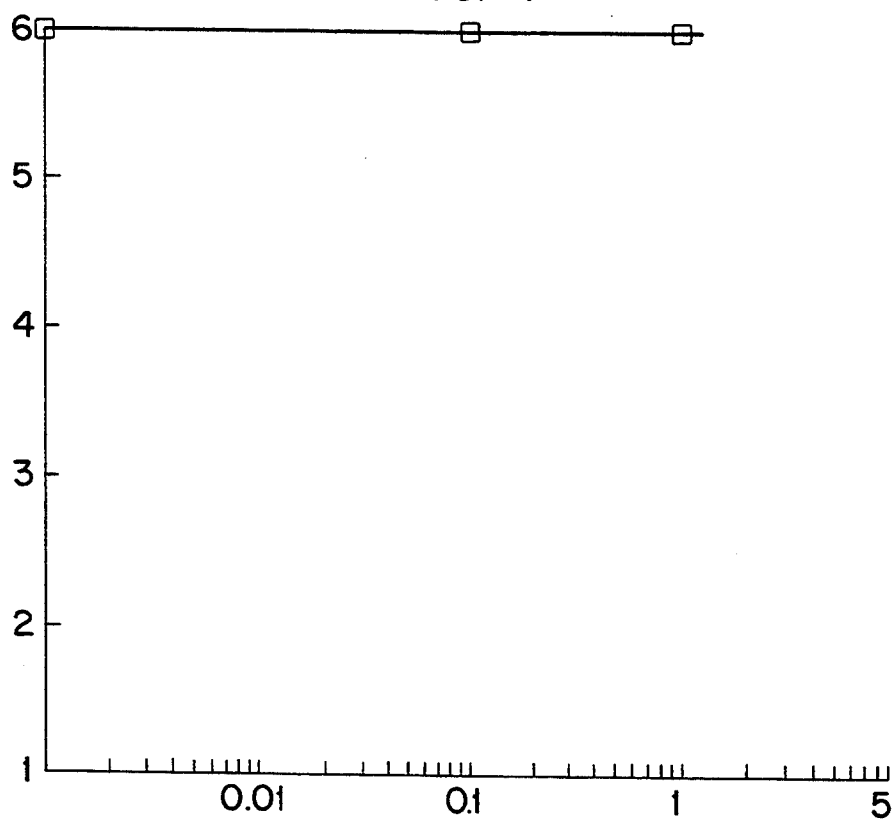

By way of comparison, FIG. 4 evidences that using a polyoxyethylene ester of undecylenic acid containing 12 ethylene oxide units, no reduction in the perception of the odor of the sludge is detected.

The curves of FIGS. 1 to 3 respectively correspond to methylundecylenate, the polyoxyethylene ester of undecylenic acid containing 8 oxyethylene units and the ester of the same acid, but containing 10 oxyethylene recurring units.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following clams, including equivalents thereof.

What is claimed is:

1. A process for deodorizing a malodorous sewage sludge, comprising treating such sewage sludge with an effective deodorizing amount of at least one alkyl ester of undecylenic acid and/or at least one polyoxyalkylene ester of undecylenic acid having from 2 to 10 oxyalkylene recurring units.

2. The process as defined by claim 1, said at least one alkyl ester of undecylenic acid having from 1 to 12 carbon atoms in the ester moiety thereof.

3. The process as defined by claim 1, said at least one undecylenic acid ester comprising a polyoxyethylene, polyoxypropylene or poly(oxyethylene)/(oxypropylene) ester of undecylenic acid.

4. The process as defined by claim 1, comprising treating such sewage sludge with from 0.01% to 5% by weight relative to the weight of the sludge to be deodorized of said at least one ester of undecylenic acid.

5. The process as defined by claim 1, comprising treating such sewage sludge with a liquid suspension or solution of said at least one ester of undecylenic acid.

6. The process as defined by claim 1, comprising treating such sewage sludge with at least one ester of undecylenic acid deposited onto a support therefor.

7. The process as defined by claim 6, said support comprising clay particulates.

8. A composition of matter comprising (a) a sewage sludge and (b) an effective sewage sludge deodorizing amount of at least one alkyl ester of undecylenic acid and/or at least one polyoxyalkylene ester of undecylenic acid having from 2 to 10 oxyalkylene recurring units.

* * * * *